United States Patent
Obara et al.

[11] Patent Number: 6,121,305
[45] Date of Patent: Sep. 19, 2000

[54] BIPYRAZOLE DERIVATIVE, AND MEDICINE OR REAGENT COMPRISING THE SAME AS ACTIVE COMPONENT

[75] Inventors: Heitaro Obara, Sendai; Takashi Igarashi, Togane; Kazuhisa Sakurai, Yachimata; Tetsuo Oi, Sakura, all of Japan

[73] Assignees: Daiichi Radioisotope Laboratories, Ltd., Tokyo; Yamagata Technopolis Foundation, Yamagata, both of Japan

[21] Appl. No.: 09/186,279

[22] Filed: Nov. 5, 1998

[51] Int. Cl.$^7$ ...................................... A01N 43/56
[52] U.S. Cl. ......................... 514/404; 548/365.4
[58] Field of Search .......................... 548/365.4; 514/404

[56] References Cited

PUBLICATIONS

Dael, *Chemical Abstracts*, vol. 125, No. 10775, 1996.
Ueda et al, *Chemical Abstracts*, vol. 98, No. 143319, 1983.
Croci et al, *Chemical Abstracts*, vol. 79, No. 65536, 1973.
Bayer, *Chemical Abstracts*, vol. 102, No. 56154, 1985.

*Primary Examiner*—Robert W. Ramsuer
*Attorney, Agent, or Firm*—Oblon, Spivak, McClelland, Maier & Neustadt, P.C.

[57] ABSTRACT

A medicine or reagent comprising a bipyrazole derivative of the following formula (I),

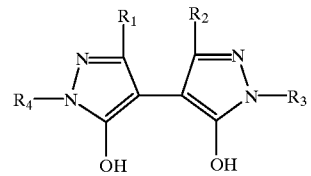

(I)

wherein $R_1$ and $R_2$ are individually a hydrogen atom, aryl group, alkyl group having 1–5 carbon atoms, or alkoxycarbonylalkyl group having a total of 3–6 carbon atoms, $R_3$ and $R_4$ are individually a hydrogen atom, alkyl group having 1–5 carbon atoms, cycloalkyl group having 5–7 carbon atoms, hydroxyalkyl group having 1–3 carbon atoms, benzyl group, naphthyl group, or substituted or unsubstituted phenyl group, as an active component. The medicine is useful for effectively capturing active oxygen and free radicals which cause adult diseases such as cerebral ischemia, heart disease, digestive system disease, and carcinoma, as well as inflammation, and for diagnosing diseases associated with in vivo free radicals.

8 Claims, 11 Drawing Sheets

BIPYRAZOLE DERIVATIVE, AND MEDICINE OR REAGENT COMPRISING THE SAME AS ACTIVE COMPONENT

BACKGROUND OF THE INVENTION

1. Field of the Invention

The present invention relates to a bipyrazole derivative and a medicine comprising the bipyrazole derivative as an active component. More particularly, the present invention relates to a bipyrazole derivative capable of capturing active oxygen and in vivo free radicals, and useful as an agent for preventing or treating various diseases induced by active oxygen or in vivo free radicals and also as a reagent for obtaining biomedical images non-invasively by way of magnetic resonance typified by ESR (Electron Spin Resonance) or for detecting active oxygen and free radicals in collected organic tissues. The present invention further relates to a medicine comprising the bipyrazole derivative as an active component.

2. Description of the Background Art

Active oxygen is defined as one type of oxygen which has a short life, but is reactive and involves in various in vivo oxidation reactions. In a narrow sense of the word, the active oxygen indicates hydroxyl radical (.OH), superoxide ($O_2^-$), singlet oxygen ($^1O_2$), and hydrogen peroxide ($H_2O_2$), while in a broad sense the active oxygen includes peroxidase radical (LOO.) and alkoxyl radical (LO.) originating from the reaction of said active factors and biological components (such as unsaturated fatty acid), and hypochlorite ($ClO^-$) which is produced from $H_2O_2$ and $Cl^-$ by the reaction with myeloperoxidase or the like. The hydroxyl radical and superoxide are radicals. "Radical" is defined as an atom or molecule which possesses one or more unpaired electrons. Although hypochlorite ion and hydrogen peroxide are not radicals themselves, these are produced by a radical reaction and induce other radical reactions. Active oxygen and radicals are generally unstable. Their life is very short, for instance, from $10^{-5}$ to $10^{-4}$ seconds in the case of benzyl radical in vapor phase, and from $10^{-3}$ to $10^{-2}$ seconds in the case of more simple radicals such as methyl radical and hydroxyl radical under ordinary pressure in vapor phase.

In recent years in the field of biology, medicine, and pharmacology, attention has been given to and studies have been undertaken relating to active oxygen and free radicals which show various in vivo physiological activities. Ultraviolet radiation, radioactive rays, air pollution, oxygen, lipid hyperoxidation, metal ions, ischemia-reperfusion, and the like can be given as the causes for in vivo formation of active oxygen and free radicals. The resulting active oxygen and in vivo free radicals induce various in vivo reactions such as hyperoxidation of lipids, denaturing of proteins, decomposition of nucleic acid, and the like. Cerebral ischemia, heart disease, digestive system disease, carcinoma, aging, inflammation, and so on can be given as the associated diseases accompanied by such reactions induced by active oxygen and in vivo free radicals. Noninvasive ex vitro detection of such active oxygen and in vivo free radicals which relate to so many diseases may help investigate the causes of a number of such diseases and provide useful medical information.

As the methods of detecting active oxygen or free radicals, there are (1) an indirect method which comprises detecting or measuring changes in absorbance or luminescence which occurs as a result of the addition of a reagent to a reaction system and (2) the ESR method in which unpaired electrons of free radicals are directly detected.

Of these, the ESR method can measure samples in the form of either solution or solid, either opaque or heterogeneous samples, so this method is very advantageous in the detection of in vivo active oxygen. However, it is difficult to measure in vivo free radicals directly by the ESR method because the in vivo free radicals are generally unstable and of short-life. In addition, active oxygen which does not have unpaired electrons cannot be measured by the ESR method.

To overcome these problems in the ESR method, a spin trap method, in which the active oxygen having unpaired electrons such as hydroxyl radicals is measured, has been developed. According to this method, a spin trap agent (T) is quickly reacted with a free radical (R.) such as a hydroxy radical having a short life as shown in the formula below. The resultant spin adduct (RT.) which is stable and has a long life is detected by the ESR method.

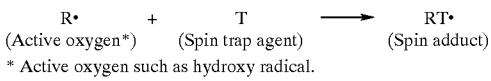

R•     +     T    ⟶    RT•
(Active oxygen*)    (Spin trap agent)     (Spin adduct)
* Active oxygen such as hydroxy radical.

Specifically, short life active oxygen can be measured by providing a compound which rapidly reacts with radicals and produces a spin adduct which is sufficiently stable for measurement by the ESR method and adding this compound to the measurement system as a spin trap agent, and measuring the stable spin adduct thus produced.

In addition, singlet oxygen which is an in vivo active oxygen and hypochlorite ion cannot be measured directly by the ESR method due to their short life and the absence of unpaired electrons. Therefore, a method analogous to the above-mentioned spin trap method is used for their measurement. The principle of this method involves the reaction of an active oxygen detection reagent (S) with an active oxygen (Q) such as singlet oxygen which does not have unpaired electrons and has a short life, whereby the former is converted into a stable free radical according to the following formula.

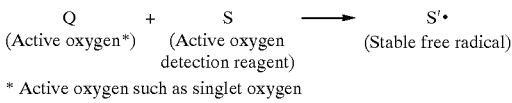

Q     +     S    ⟶    S'•
(Active oxygen*)    (Active oxygen detection reagent)     (Stable free radical)
* Active oxygen such as singlet oxygen Measurement of a short life active oxygen having no unpaired electrons becomes possible by measuring a stable free radical (S'.).

Therefore, the compound which is used as a spin trap agent or active oxygen detection reagent must satisfy the following conditions: ① to rapidly react with active oxygen and free radicals, ② to be converted into a sufficiently stable radical, ③ to be chemically stable during handling, and ④ to have low toxicity.

There are nitrone-type and nitroso-type compounds conventionally used as typical trap agents for the studies of in vivo free radicals. As nitron-type compounds, a cyclic nitron compound such as DMPO (5,5-dimethyl-1-pyrroline-1-oxide) and a linear nitron compound such as PBN (N-tert-butyl-α-phenylnitrone) can be given. As nitroso-type, DBNBS (sodium 3,5-dibromo-4-nitrosobenzenesulfonate) has been used. As an active oxygen detection reagent, TMPD (2,2,6,6-tetramethyl-4-piperidone) has been used. These are only compounds which have conventionally been used. However, none of them satisfy the above-mentioned conditions (see, e.g. Pharmacia, 28, 1347–1352 (1992)).

There is a strong demand for the prevention and treatment of adult diseases such as cerebral ischemia, heart disease, digestive system disease, and carcinoma, and prevention treatment of inflammation, as well as prevention of aging. Active oxygen and free radicals are known to cause these diseases. Therefore, the development of a medicine which can capture these factors and effectively prevent or treat these diseases has been desired.

As mentioned above, if there is a compound which can rapidly react with the active oxygen or in vivo free radicals and produce a stable reaction product, such a compound can be utilized as an active oxygen detection reagent in the ESR method which is a non-invasive measuring method. Such a compound will be useful in the diagnosis of diseases associated with active oxygen and in vivo free radicals such as carcinoma, ischemia, inflammation, and the like by utilizing biological spectrum or biological images of the active oxygen and in vivo free radicals.

The inventors of the present invention have conducted extensive studies in order to solve the above-mentioned problems and to find a pharmaceutically safe compound which rapidly reacts with active oxygen or in vivo free radicals and produces a reaction product which is stable. As a result, the inventors have found that bipyrazole derivatives which possess a bipyrazole structure and two hydroxyl groups as shown by the following formula (I) satisfy the above-mentioned conditions and function as an active oxygen detection reagent.

The inventors have discovered that these derivatives can capture active oxygen and in vivo free radicals, and is useful as a medicine for preventing or treating such diseases as cerebral ischemia, heart disease, digestive system disease, carcinoma, aging, and inflammation, and also as a diagnostic agent or detection reagent such as a spin trap agent. These findings have led to the completion of the present invention.

SUMMARY OF THE INVENTION

Accordingly, an object of the present invention is to provide a medicine or reagent useful as an active oxygen or free radical capturing agent, which comprises a bipyrazole derivative of the following formula (I),

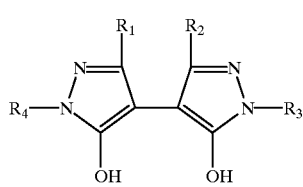

(I)

wherein $R_1$ and $R_2$ are individually a hydrogen atom, aryl group, alkyl group having 1–5 carbon atoms, or alkoxycarbonylalkyl group having a total of 3–6 carbon atoms, $R_3$ and $R_4$ are individually a hydrogen atom, alkyl group having 1–5 carbon atoms, cycloalkyl group having 5–7 carbon atoms, hydroxyalkyl group having 1–3 carbon atoms, benzyl group, naphthyl group, or substituted or unsubstituted phenyl group, as an active component.

Another object of the present invention is to provide a bipyrazole derivative of the following formula (I'),

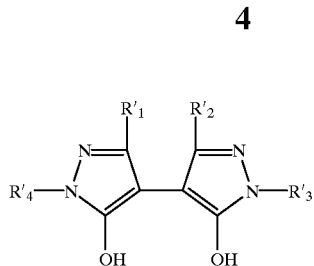

(I')

wherein $R_1'$ and $R_2'$ are individually a hydrogen atom, aryl group, alkyl group having 1–5 carbon atoms, or alkoxycarbonylalkyl group having a total of 3–6 carbon atoms, $R_3'$ and $R_4'$ are individually a hydrogen atom, alkyl group having 1–5 carbon atoms, cycloalkyl group having 5–7 carbon atoms, hydroxyalkyl group having 1–3 carbon atoms, benzyl group, naphthyl group, or substituted or unsubstituted phenyl group, provided that when both the groups $R_1'$ and $R_2'$ are a methyl group or ethoxycarbonyl group, $R_3'$ and $R_4'$ are not an unsubstituted phenyl group simultaneously, and further provided that when both the groups $R_1'$ and $R_2'$ are a hydrogen atom, $R_3'$ and $R_4'$ are not a hydrogen atom simultaneously.

Other and further objects, features and advantages of the present invention will appear more fully from the following description.

DETAILED DESCRIPTION OF THE INVENTION AND PREFERRED EMBODIMENTS

Figure 1:
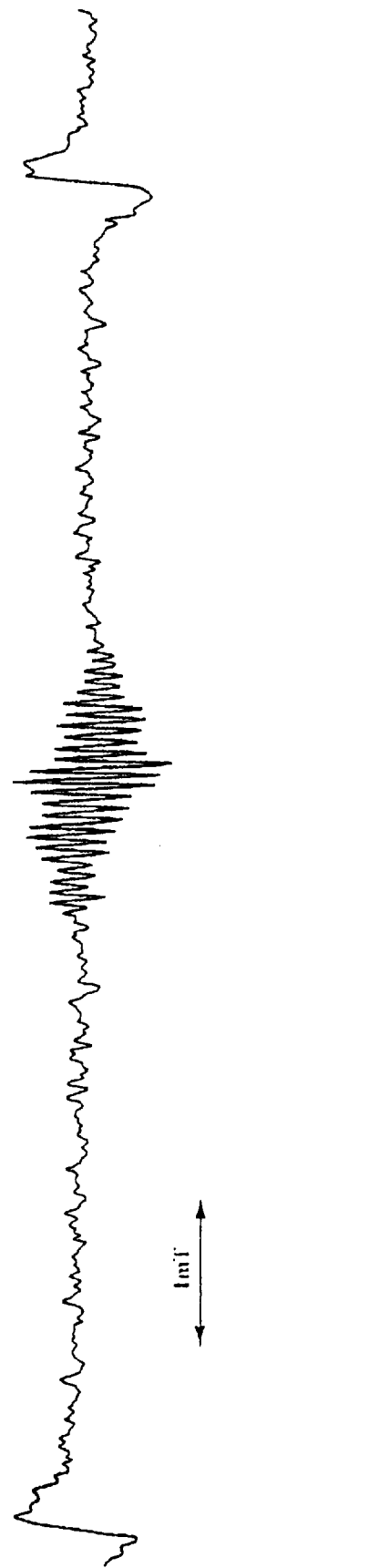
FIG. 1 shows a spin adduct ESR spectrum of excitation hematoporphyrin-singlet oxygen generation system in the presence of 5,5'-dihydroxy-3,3'-dimethyl-1,1'-diphenyl-4,4'-bipyrazole as a test compound.

Among the bipyrazole derivatives of the present invention, the compounds with a methyl group or ethoxycarbonyl group for both the groups $R_1$ and $R_2$ in the formula (I) and with an unsubstituted phenyl for both the groups $R_3$ and $R_4$, and the compounds having a hydrogen atom for all of the groups $R_1$–$R_4$ are known compounds. All other bipyrazole derivatives of the present invention are novel compounds.

Alkyl groups having 1–5 carbon atoms can be given as preferred examples for $R_1$ and $R_2$ in the bipyrazole derivatives (I) of the present invention. Of these alkyl groups, methyl group is particularly preferred. As a preferred group for $R_3$ and $R_4$, phenyl group can be given. The phenyl group may be either substituted or not substituted. As examples of the substituents, an alkyl group, alkoxyl group, hydroxyalkyl group, alkoxycarbonyl group, alkylmercapto group, alkylamino group, dialkylamino group, halogen atom, trifluoromethyl group, nitro group, amino group, cyano group, hydroxyl group, carboxyl group, acetamide group, and the like are given. The phenyl group may be substituted by one of these groups or two or three of these groups which may be either the same or different each other.

The bipyrazole derivative (I) of the present invention can be prepared from a combination of an acrylic acid derivative (IIa) and a hydrazine derivative (IIIa) and a combination of an acrylic acid derivative (IIb) and a hydrazine derivative (IIIb) by condensation with heating according to the following reaction scheme. The resulting pyrazolidone compounds (IVa) and (IVb) are optionally purified and reacted in the presence of a catalyst such as selenium dioxide and an oxidant such as hydrogen peroxide to obtain the bipyrazole derivative (I):

wherein $R_1$, $R_2$, $R_3$, and $R_4$ have the same meanings as defined above.

The condensation reactions of the compound (IIa) or (IIb) and the compound (IIIa) or (IIIb) are carried out at a temperature of about 80–140° C. for about 1–5 hours. The oxidation and bonding reaction of the compounds (IVa) and (IVb) are carried out at a temperature of about 0–80° C. for about 3 to 24 hours.

The compounds (IIa) and (IIb) and the compounds (IIIa) and (IIIb) which are starting materials for the above-mentioned reactions are either known compounds or the compounds which can be easily prepared by known processes. The compounds (IIa) and (IIb) and the compounds (IIIa) and (IIIb) may be respectively either the same or different in the present invention.

In the above process, the compound (IV) must not necessarily be purified. When the compound is purified, known purification methods such as filtration, drying under reduced pressure, recrystallization, and the like can be utilized. In addition, when any substituent among $R_1$ to $R_4$ is denatured by oxidation, such a substituent should be protected according to a conventional method prior to the reaction. For example, when the substituent $R_3$ or $R_4$ for the hydrazine derivative (III) is an aminophenyl group or mercaptophenyl group, these groups should be converted into a known protected amino group or mercapto group, respectively, prior to the reaction.

The bipyrazole derivative (I) thus obtained is further purified, if required, and made into any appropriate preparations by a conventional method for use as a medicine or reagent.

Specifically, the medicine of the present invention can be utilized as a free radical scavenger for prevention and medical treatment of diseases in which free radicals are involved, such as cerebral ischemia, heart disease, digestive system disease, carcinoma, aging, and inflammation.

For this objective, the compound of the present invention can be made into preparations for oral or parenteral administration, together with pharmaceutically acceptable known carriers, for example, solid carriers such as lactose,

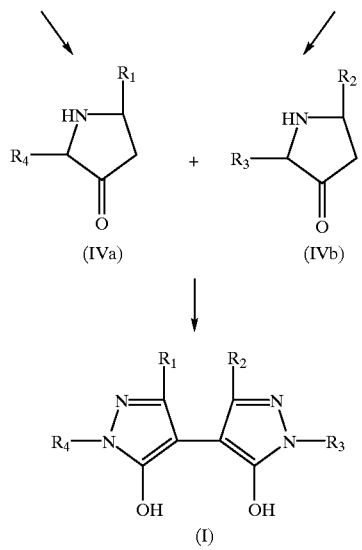

sucrose, crystalline cellulose, talc, stearic acid, lecitin, sodium chloride, and inositol, and liquid carriers such as sirup, glycerol, olive oil, ethanol, benzyl alcohol, propylene glycol, water, and the like.

Moreover, the medicine of the present invention can be used as a reagent for non-invasively producing biological images or for detecting active oxygen and free radicals in collected organism tissues by a magnetic resonance method typified by the ESR method.

Although the reason for the compound of the present invention reacting with active oxygen and in vivo free radicals to produce a stable substance is not completely made clear, a most probable reason may be the formation of a stable radical due to the reaction of the active oxygen and free radicals by oxidation according to the following formula.

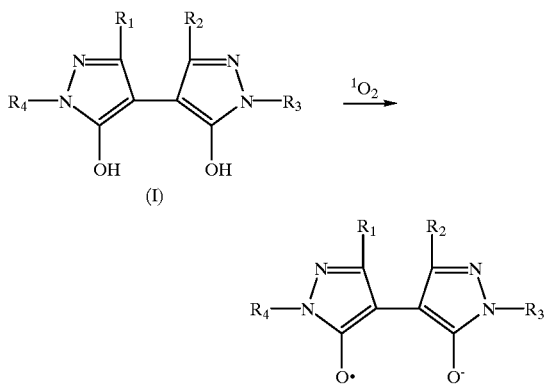

Because the compound of the present invention is converted into a stable substance by the reaction with active oxygen or in vivo free radicals as mentioned above, the compound is expected to be useful as an agent for the prevention or medical treatment of the diseases caused by the active oxygen or in vivo free radicals, as a medicine to produce images of the active oxygen and in vivo free radicals by the ESR method, or as a detection reagent.

Specifically, the ESR method is a type of magnetic resonance method, in which the subjects of detection are unpaired electrons of atoms and molecules. Free radicals such as active oxygen and transition elements possess unpaired electrons, both being the subjects of measurement by the ESR method. As the relationship between the active oxygen and physiological functions became clear in recent years, the ESR has come to be utilized for the identification of active oxygen and the analysis of the oxidation-reduction reactions.

Although X-band (about 9.5 GHz) microwaves have been used in the ESR measurement heretofore, the method could not measure a large amount of in vivo biological samples because of a large dielectric loss due to water. However, the recent development of ESR equipment using the microwaves called L-band (1 GHz or less) has made it possible to non-invasively measure samples containing a large amount of water and free radicals in biological samples (see, e.g. Pharmacia, 27, 710–715 (1991)). Thus, there is now a prospect that a large amount of in vivo biological samples such as humans can be measured by this method.

The compound of the present invention is thus expected to be useful as a detection reagent in the ESR method using ESR equipment for use with humans, whereby active oxygen and free radicals in human bodies can be non-invasively measured and useful information relating to the diseases and symptoms caused by the active oxygen and the free radicals can be provided.

The present invention will now be described by way of examples, which should not be construed as limiting of the present invention.

EXAMPLES

Example 1

Synthesis of 5,5'-dihydroxy-3,3'-dimethyl-1,1'-diphenyl-4,4'-bipyrazole (1) Synthesis of 3-methyl-1-phenyl-5-pyrazolidone 17.2 g of crotonic acid (MW 86.09, 0.2 mol) was added to 21.6 g of phenylhydrazine (MW 108.14, 0.2 mol), and the mixture was stirred for one hour while heating at 150–160° C. The reaction solution was dissolved in 500 ml of ether. The solution was washed twice with 100 ml of 10% aqueous solution of sodium hydroxide and once with 100 ml of water, followed by evaporation of the ether. The resulting solid was dried under reduced pressure and recrystallized from toluene to obtain 20.31 g of 3-methyl-1-phenyl-5-pyrazolidone (MW 176.0, 0.126 mol, 58%).

(2) Synthesis of 5,5'-dihydroxy-3,3'-dimethyl-1,1'-diphenyl-4,4'-bipyrazole 11.4 g of 3-methyl-1-phenyl-5-pyrazolidone (64.8 mmol) obtained in (1) above was dissolved in 200 ml of methanol. A sufficient amount of nitrogen gas was injected into the solution to replace the air with nitrogen.

A catalytic amount of selenium dioxide (330 mg, 0.05 equivalent, MW 110.96) was added and 21 ml (3 equivalent) 30% hydrogen peroxide was added dropwise over an ice-cooled water bath. The mixture was allowed to settle at room temperature, followed by further stirring for 24 hours. The deposited crystals were separated by filtration and dried under reduced pressure to obtain 5.57 g of 5,5'-dihydroxy-3,3'-dimethyl-1,1'-diphenyl-4,4'-bipyrazole (MW 346, 12.4 mmol, 49.7%).

Melting point: above 280° C.

NMR (δ ppm):

7.77, 7.76(d, 2H), 7.48, 7.46, 7.45(tr, 4H), 7.25, 7.24, 7.22 (tr, 4H), 2.51, 2.50, 2.50 (m, 2H), 2.16 (s, 6H)

Mass spectrum: 346 m/z EI+

Example 2

Synthesis of 5,5'-dihydroxy-3,3'-dimethyl-1,1'-bis(4-carboxyphenyl)-4,4'-bipyrazole (1) Synthesis of 3-methyl-1-(4-carboxyphenyl)-5-pyrazolidone 2.83 g of 5 equivalent crotonic acid (MW 86.09, 32.9 mmol) was added to 1 g of 4-carboxyphenyl hydrazine (MW 152.15, 6.57 mmol), and the mixture was stirred for two hours at 130–140° C.

After removing the unreacted crotonic acid which was sublimated, the reaction product was recrystallized from 20 ml of methanol to obtain 570 mg of 3-methyl-1-(4-carboxyphenyl)-5-pyrazolidone (MW 220, 2.59 mmol, 39.4%).

(2) Synthesis of 5,5'-dihydroxy-3,3'-dimethyl-1,1'-bis(4-carboxyphenyl)-4,4'-bipyrazole 1 g of 3-methyl-1-(4-carboxyphenyl)-5-pyrazolidone (4.5 mmol) was dissolved in 20 ml of methanol and a sufficient amount of nitrogen gas was injected into the solution to replace the air with nitrogen. A catalytic amount of selenium dioxide (25 mg, 0.05 equivalent, MW 110.96) was added and 1.5 ml (3 equivalent) 30% hydrogen peroxide was added dropwise over an ice-cooled water bath. The mixture was stirred until room temperature. The stirring was continued for a further 12 hours while heating at 70–80° C. The deposited crystals were separated by filtration and dried under reduced pressure to obtain 460 mg of 5,5'-dihydroxy-3,3'-dimethyl-1,1'-bis(4-carboxyphenyl)-4,4'-bipyrazole (MW 434.12, 1.06 mmol, 47.1%).

Melting point: above 280° C.

NMR (δ ppm):

12.85(brs, 1H), 11.45(brs, 1H), 8.02, 8.01, 7.94,7.92 (dd, 8H), 2.50, 2.49, 2.49, 2.48 (m, 2H), 2.13(s, 6H)

Mass spectrum: 435.2 m+1/Z Positive FAB

Example 3

The experiments were carried out in the same manner as in Example 1(1), except for using the raw materials (a) in the following Table 1 instead of phenylhydrazine to produce products (b) in the right column of Table 1.

TABLE 1

| Raw material (a) | Product (b) |
| --- | --- |
| p-methylphenylhydrazine | 3-methyl-1-(4-methylphenyl)-5-pyrazolidone |
| p-methoxyphenylhydrazine | 3-methyl-1-(4-methoxyphenyl)-5-pyrazolidone |
| P-chlorophenylhydrazine | 3-methyl-1-(4-chlorophenyl)-5-pyrazolidone |
| 4-hydrazinobenzoic acid | 4-(3-methyl-5-pyrazolidone)benzoic acid |
| 4-hydrazinobenzenesulfonic acid | 4-(3-methyl-5-pyrazolidone)benzenesulfonic acid |
| ethyl 4-hydrazinobenzoate | ethyl 4-(3-methyl-5-pyrazolidone)benzoate |
| p-hydroxyphenylhydrazine | 3-methyl-1-(4-hydroxyphenyl)-5-pyrazolidone |
| hydrazine | 3-methyl-5-pyrazolidone |
| hydroxyethylhydrazine | 3-methyl-1-hydroxyethyl-5-pyrazolidone |

Example 4

The experiments were carried out in the same manner as in Example 1(1), except for using the raw materials (c) in the following Table 2 instead of crotonic acid to produce the products (d) in the right column of Table 2.

TABLE 2

| Raw material (C) | Product (d) |
| --- | --- |
| Acrylic acid | 1-phenyl-5-pyrazolidone |
| β-phenylacrylic acid | 1,3-diphenyl-5-pyrazolidone |

Example 5

(A) The experiments were carried out in the same manner as in Example 1(2), except for using 11.4 g of the raw materials (b) in the following Table 3, instead of 11.4 g of 3-methyl-1-phenyl-5-pyrazolidone, to produce the target compounds (e) in the right column of Table 3.

TABLE 3

| Raw materials (b) | Target compound (e) |
| --- | --- |
| 3-methyl-1-(4-methylphenyl)-5-pyrazolidone | 5,5'-dihydroxy-3,3'-dimethyl-1,1'-bis(4-methylphenyl)-4,4'-bipyrazole |
| 3-methyl-1-(4-methoxyphenyl)-5-pyrazolidone | 5,5'-dihydroxy-3,3'-dimethyl-1,1'-bis(4-methoxyphenyl)-4,4'-bipyrazole |
| 3-methyl-1-(4-chlorophenyl)-5-pyrazolidone | 5,5'-dihydroxy-3,3'-dimethyl-1,1'-bis(4-chlorophenyl)-4,4'-bipyrazole |
| 4-(3-methyl-5-pyrazolidone)benzoic acid | 5,5'-dihydroxy-3,3'-dimethyl-1,1'-bis(4-carboxyphenyl-4,4'-bipyrazole |
| 4-(3-methyl-5-pyrazolidone)benzenesulfonic acid | 5,5'-dihydroxy-3,3'-dimethyl-1,1'-bis(4-sulfophenyl)-4,4'-bipyrazole |
| ethyl 4-(3-methyl-5-pyrazolidone)benzoate | 5,5'-dihydroxy-3,3'-dimethyl-1,1'-bis(4-ethoxycarbonylphenyl)-4,4'-bipyrazole |
| 3-methyl-1-(4-hydroxydiphenyl)-5-pyrazolidone | 5,5'-dihydroxy-3,3'-dimethyl-1,1'-bis(4-hydroxyphenyl)-4,4'-bipyrazole |
| 3-methyl-5-pyrazolidone | 5,5'-dihydroxy-3,3'-dimethyl-4,4'-bipyrazole |
| 3-methyl-1-hydroxyethyl-5-pyrazolidone | 5,5'-dihydroxy-3,3'-dihydroxyethyl-4,4'-bipyrazole |

(B) The experiments were carried out in the same manner as in Example 1(2), except for using 11.4 g of the raw materials (d) in the following Table 4 instead of 11.4 g of 3-methyl-1-phenyl-5-pyrazolidone to produce the target compounds (e) in the right column of Table 4.

TABLE 4

| Raw material (d) | Target compound (e) |
| --- | --- |
| 1-phenyl-5-pyrazolidone | 5,5'-dihydroxy-1,1'-diphenyl-bipyrazole |
| 1,3-diphenyl-5-pyrazolidone | 5,5'-diydroxy-1,1',3,3'-tetraphenyl-4,4'-bipyrazole |

Example 6

Singlet Oxygen Capturing Test

Singlet oxygen capturing capability of the compound of the present invention was examined using a system, wherein two types of photosensitizing compounds known as singlet oxygen generators, one light excitation riboflavin and the other light excitation hematoporphyrin, were used.

Specifically, these photosensitizing compounds are known to take a triplet excited state by absorbing visible rays, and the excitation energy is transferred to the dissolved oxygen, thereby producing a singlet oxygen (see, e.g. "Free radical and organism (Institute Publication Center)"). The singlet oxygen itself can not be measured by the ESR method, because this is not a free radical. However, if there is a compound which reacts with the singlet oxygen to produce a stable radical in the system, it is possible to measure the singlet oxygen by the ESR method.

Therefore, if the compound of the present invention has the capability of reacting with the singlet oxygen and producing a stable radical, the singlet oxygen can be measured by the ESR method using the compound.

In this example, the singlet oxygen produced by the light excitation riboflavin system and the light excitation hematoporphyrin system was measured by the X-band ESR method as follows.

Reagents (1) 1.67 mM hematoporphyrin solution:
   A solution prepared by dissolving 1 mg of hematoporphyrin in 1 ml of a phosphate buffered saline solution (hereinafter called "Reagent A").

(2) 0.18 mM riboflavin solution:
   A solution prepared by dissolving 67 μg of riboflavin in 1 ml of a phosphate buffered saline solution (hereinafter called "Reagent B").

(3) Phosphate buffered saline solution (pH 7.4):
   Dulbecco's phosphate buffered saline (not containing calcium ion and magnesium ion): a solution prepared by dissolving 9.6 g of "Nissui" powder in 1000 ml of distilled water (hereinafter called "Reagent C").

(4) Test solutions:
   Sample A: A solution prepared by dissolving 0.8 mg of 5,5'-dihydroxy-3,3'-diphenyl-4,4'-bipyrazole in 1 ml of sodium hydroxide aqueous solution with a concentration of 0.36 mg/ml(hereinafter called "Test Solution A").
   Sample B: A solution prepared by dissolving 1 mg of 5,5'-dihydroxy-3,3'-dimethyl-1,1'-bis(4-carboxyphenyl)-4,4'-bipyrazole in 1 ml of phosphate buffered saline solution (hereinafter called "Test Solution B").

Measurement Systems

① Excitation Hematoporphyrin System
   50 μl of Reagent A, 100 μl of Reagent C, and 50 μl of Test Solutions A or B were added to a microplate and the mixture was stirred. The reaction mixture was suctioned into a flat cell (manufactured by Labotech Co.) and irradiated by a fluorescent lamp for 90 seconds to measure the ESR spectrum.

② Excitation Riboflavin System
   60 μl of Reagent B, 100 μl of Reagent C, and 40 μl of Test Solutions A or B were added to a microplate and the mixture was stirred. The reaction mixture was suctioned into a flat cell (manufactured by Labotech Co.) and irradiated by a fluorescent lamp for 60 seconds to measure the ESR spectrum.

Control Measurement Systems (Containing No Test Samples)

① Excitation hematoporphyrin system
   50 μl of Reagent A and 150 μl of Reagent C were added to a microplate and the mixture was stirred. The reaction mixture was suctioned into a flat cell (manufactured by Labotech Co.) and irradiated by a fluorescent lamp for 90 seconds to measure the ESR spectrum.

② Excitation Riboflavin System
   60 μl of Reagent B and 140 μl of Reagent C were added to a microplate and the mixture was stirred. The reaction mixture was suctioned into a flat cell (manufactured by Labotech Co.) and irradiated by a fluorescent lamp for 60 seconds to measure the ESR spectrum.

Comparative Measurement System (Containing No Singlet Oxygen Generation Source)
   150 μl of Reagent C and 50 μl of Test Solution A or B were added to a microplate and the mixture was stirred. The reaction mixture was suctioned into a flat cell (manufactured by Labotech Co.) and irradiated by a fluorescent lamp for 90 seconds to measure ESR spectrum.

Figure 2:
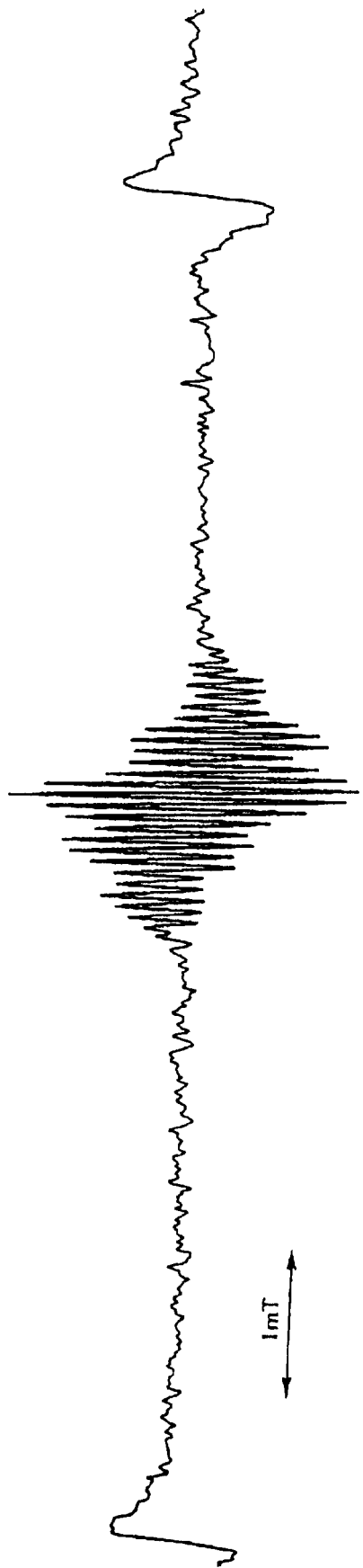
FIG. 2 shows a spin adduct ESR spectrum of excitation hematoporphyrin-singlet oxygen generation system in the presence of 5,5'-dihydroxy-3,3'-dimethyl-1,1'-bis(4-carboxyphenyl)-4,4'-bipyrazole as a test compound.
Figure 3:
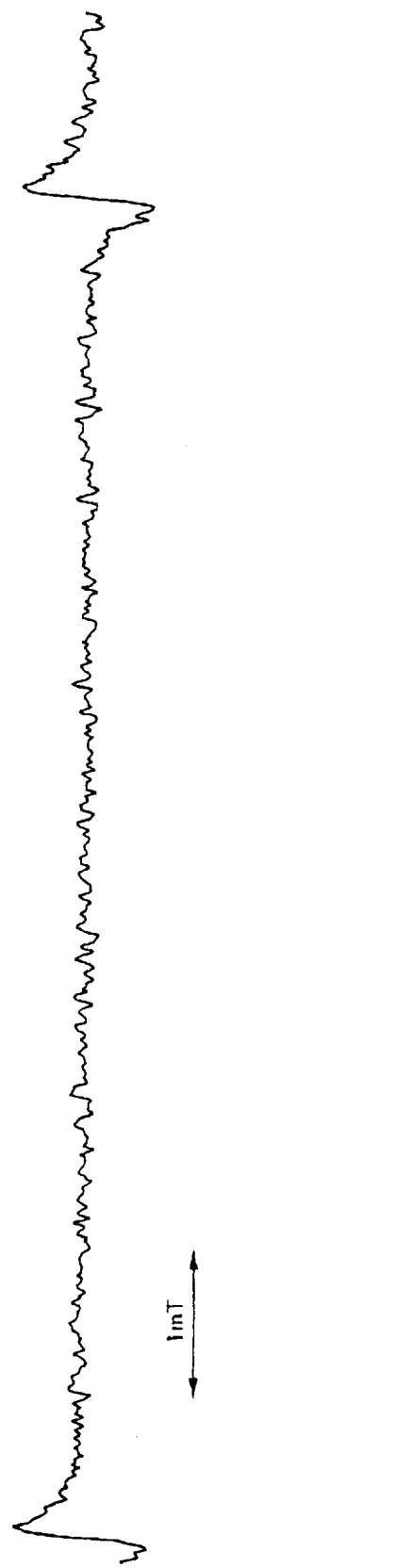
FIG. 3 shows an ESR spectrum of excitation hematoporphyrin-singlet oxygen generation system in the absence of a test compound.

Measurement Conditions of ESR Spectrum
   ESR was measured under the following conditions.
   Measurement device: An electron spin resonance equipment, JES-RE1X (JEOL Ltd.)
   Magnetic field: 337.5±5 mT
   Magnetic field modulation: 100 KHz
   Modulation width: 0.032 mT
   Time constant: 0.1 second
   Microwave power: 20 mW
   Sweep time: two minutes
   Measurement temperature: room temperature Results The ESR spectrum in the measurement system containing the test sample A and the excitation hematoporphyrin as a singlet oxygen source (the measurement system ①) and the ESR spectrum in the measurement system containing the test sample B and the excitation hematoporphyrin as a singlet oxygen source (the measurement system ①) are respectively shown in FIGS. 1 and 2. ESR signals are clearly recognized in these ESR spectrums. On the other hand, no ESR signals were seen in FIG. 3, which shows the ESR spectrum for the control measurement system ① which contains excitation hematoporphyrin as a singlet oxygen source, but does not contain a test sample.

Figure 4:
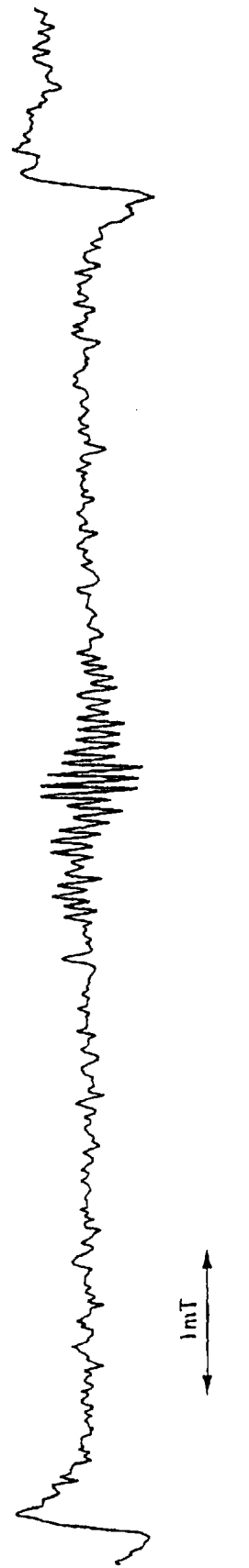
FIG. 4 shows a spin adduct ESR spectrum of excitation riboflavin-singlet oxygen generation system in the presence of 5,5'-dihydroxy-3,3'-dimethyl-1,1'-diphenyl-4,4'-bipyrazole as a test compound.
Figure 5:
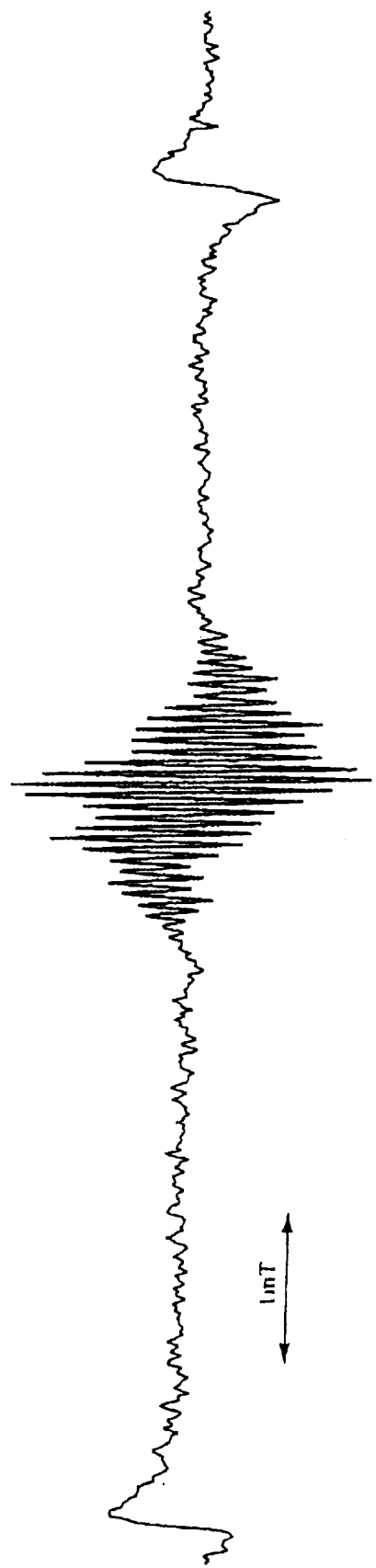
FIG. 5 shows a spin adduct ESR spectrum of excitation riboflavin-singlet oxygen generation system in the presence of 5,5'-dihydroxy-3,3'-dimethyl-1,1'-bis(4-carboxyphenyl)-4,4'-bipyrazole as a test compound.

The ESR spectrum in the measurement system containing the Test Solution A and the excitation riboflavin as a singlet oxygen source (the measurement system ②) and the ESR spectrum in the measurement system containing test sample B and the excitation riboflavin as a singlet oxygen source (the measurement system ②) are respectively shown in FIGS. 4 and 5. ESR signals are clearly recognized in these ESR spectrums. On the other hand, the ESR spectrum for the control measurement system ② which contains excitation riboflavin as a singlet oxygen source, but does not contain a sample was similar to the spectrum of FIG. 3, exhibiting no ESR signals.

Furthermore, no ESR signals were recognized in the ESR spectrums for the system containing test sample A but not containing a singlet oxygen producing reagent (Comparative Measurement System) and the system containing test sample B but not containing a singlet oxygen producing reagent (Comparative Measurement System).

As clear from these results, the systems containing test sample A or B and a singlet oxygen generating source produced strong signals due to the formation of stable free radicals from the test sample A or B by the reaction with singlet oxygen. In contrast, the system which contains a singlet oxygen generating source, but does not contain test sample A or B (Control Measurement System) produced no signals, because no stable free radicals were formed in this system. In the systems which contain test sample A or B, but do not contain a singlet oxygen generating source (Comparative Measurement Systems), no signals were recognized, because no singlet oxygen was produced in these systems.

Based on the above results, 5,5'-dihydroxy-3,3'-dimethyl-1,1'-diphenyl-4,4'-bipyrazole and 5,5'-dihydroxy-3,3'-dimethyl-1,1'-bis(4-carboxyphenyl)-4,4'-bipyrazole which are the compounds of the present invention were confirmed to effectively capture short life active oxygen (singlet oxygen, $^1O_2$).

Example 7

Hypochlorite Ion Capturing Test

Hypochlorite ion capturing ability of the compounds of the present invention was examined using a system which is established as the system of generating active oxygen as hypochlorite ion.

Reagents
(1) 67 μM sodium hypochlorite aqueous solution
   A solution prepared by diluting 5% sodium hypochlorite aqueous solution (Pr. G standard, manufactured by Wako Pure Chemical Industries, Ltd.) to a 10,000-fold with distilled water (hereinafter called "Reagent ①").

(2) Phosphate buffered saline solution (pH 7.4):

Dulbecco's phosphate buffered saline (not containing calcium ion and magnesium ion): a solution prepared by dissolving 9.6 g of "Nissui" powder in 1000 ml of distilled water (hereinafter called "Reagent ②").

(3) Test solutions:

Sample A: A solution prepared by dissolving 0.8 mg of 5,5'-dihydroxy-3,3'-diphenyl-4,4'-bipyrazole in 1 ml of sodium hydroxide aqueous solution with a concentration of 0.36 mg/ml (hereinafter called "Test Solution A").

Sample B: A solution prepared by dissolving 1 mg of 5,5'-dihydroxy-3,3'-dimethyl-1,1'-bis(4-carboxyphenyl)-4,4'-bipyrazole in 1 ml of phosphate buffered saline solution (hereinafter called "Test Solution B").

Measurement System

50 μl of Test Solution A or B, 140 μl of Reagent ②, and 10 μl of Reagent ① were added to a microplate, and the mixture was stirred. The reaction mixture was suctioned into a flat cell (manufactured by Labotech Co.) and filled into the ESR equipment. A magnetic field sweep was initiated 30 seconds after the stirring.

Comparative Measurement System (Not Containing Hypochlorite)

50 μl of Test Solution A or B, 140 μl of Reagent ②, and 10 μl of distilled water were added to a microplate, and the mixture was stirred. The reaction mixture was suctioned into a flat cell (manufactured by Labotech Co.) and filled into the ESR equipment. A magnetic field sweep was initiated 30 seconds after the stirring.

Control Measurement System (Containing No Test Sample)

10 μl of Reagent ① and 190 μl of Reagent ② were added to a microplate, and the mixture was stirred. The reaction mixture was suctioned into a flat cell (manufactured by Labotech Co.) and the ESR spectrum was measured.

Measurement Conditions of ESR Spectrum

ESR was measured under the following conditions.

Measurement device: An electron spin resonance equipment, JES-RE1X (JEOL Ltd.)

Magnetic field: 337.5±5 mT

Magnetic field modulation: 100 KHz

Modulation width: 0.032 mT

Time constant: 0.1 second

Microwave power: 20 mW

Sweep time: two minutes

Measurement temperature: room temperature

Results

Figure 6:
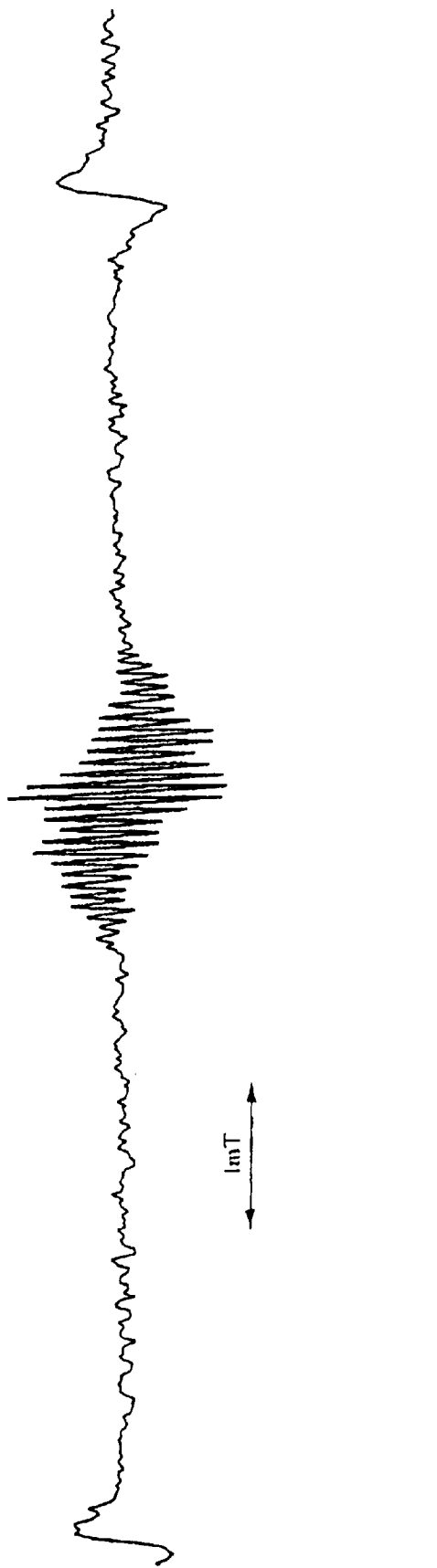
FIG. 6 shows an ESR spectrum of a system wherein hypochlorite ion is generated in the presence of 5,5'-dihydroxy-3,3'-dimethyl-1,1'-diphenyl-4,4'-bipyrazole as a test compound.
Figure 7:
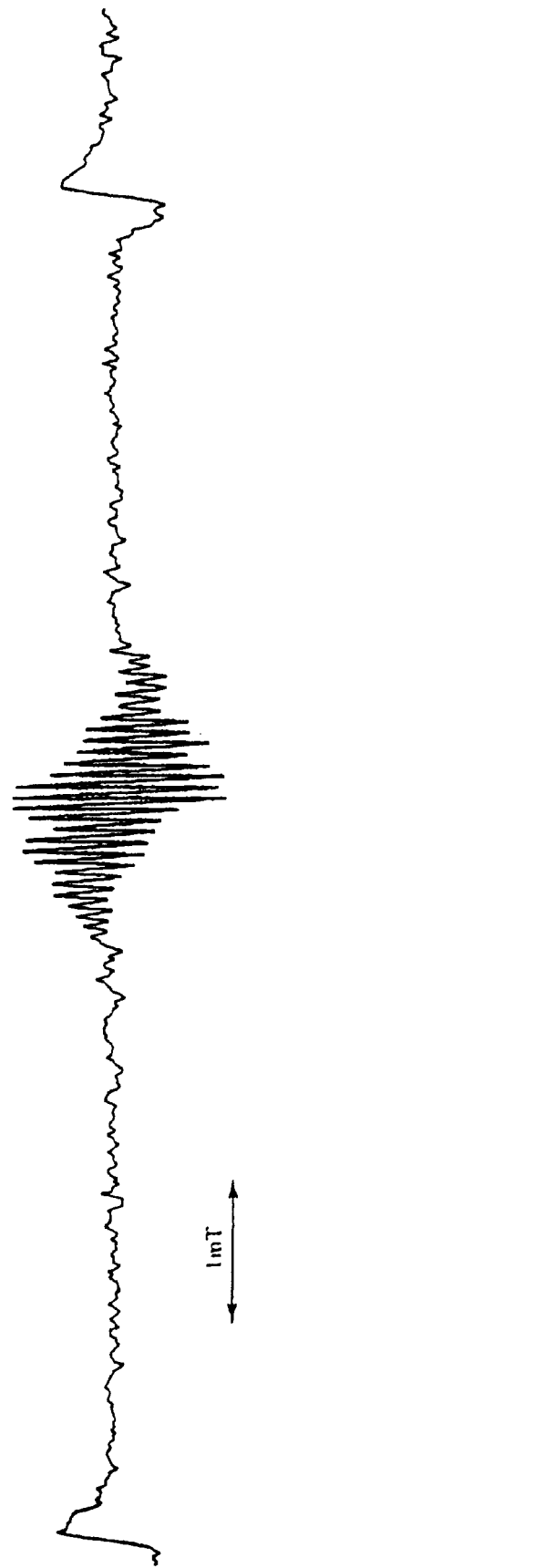
FIG. 7 shows an ESR spectrum of a system wherein hypochlorite ion is generated in the presence of 5,5'-dihydroxy-3,3'-dimethyl-1,1'-bis(4-carboxyphenyl)-4,4'-bipyrazole as a test compound.

The ESR spectrum in the system in which Sample A was included and hypochlorite ion was generated (Measurement System) and the ESR spectrum in which Sample B was included and hypochlorite ion was generated (Measurement System) are respectively shown in FIGS. 6 and 7. The ESR signals are clearly recognized in these ESR spectrums.

On the other hand, the ESR spectrum for the system in which Sample A was included but no hypochlorite ion was generated (Comparative Measurement System) and the ESR spectrum for the system in which Sample B was included but no hypochlorite ion was generated (Comparative Measurement System) exhibited no ESR signals. The ESR signals were also not seen in the ESR spectrum for the system which contains no sample but wherein hypochlorite ion was generated (Control Measurement System).

As it is clear from these results, strong signals were obtained in the Measurement Systems, because Sample A or Sample B reacts with hypochlorite ion to produce stable radicals. In contrast, no signals were produced in the Comparative Measurement Systems, because no stable radicals were produced in the absence of hypochlorite ion. Also, no signals were produced in the Control Measurement System, because no stable radicals were produced in the absence of the sample compound.

Based on the above results, 5,5'-dihydroxy-3,3'-dimethyl-1,1'-diphenyl-4,4'-bipyrazole and 5,5'-dihydroxy-3,3'-dimethyl-1,1'-bis(4-carboxyphenyl)-4,4'-bipyrazole which are the compounds of the present invention were confirmed to effectively capture active oxygen (hypochlorite ion, $OCl^-$).

Example 8

<Comparison of Singlet Oxygen Detection Sensitivity of Known Active Oxygen Detection Reagents and the Compound of the Present Invention>

The singlet oxygen detection sensitivity of the 5,5'-dihydroxy-3,3'-dimethyl-1,1'-diphenyl-4,4'-bipyrazole which is the compound of the present invention and 2,2,6,6-tetramethyl-4-piperidone (TMPD) was compared using an X-band ESR at around the neutral pH region. The TMPD is known to react with singlet oxygen and other active oxygen and to be transformed into a stable radical. This compound is conventionally used as a detection reagent for singlet oxygen.

Reagents (1) 1.67 mM hematoporphyrin solution:

A solution prepared by dissolving 1 mg of hematoporphyrin in 1 ml of a phosphate buffered saline solution with pH 7.4 (hereinafter called "Reagent ③").

(2) Test solution ①

A solution prepared by dissolving 2 mg of 5,5'-dihydroxy-3,3'-dimethyl-1,1'-diphenyl-4,4'-bipyrazole in 1 ml of dimethyl sulfoxide (5.8 mM).

(3) Test solution ②

A TMPD solution: A solution prepared by dissolving 1 mg of TMPD in 1 ml of dimethyl sulfoxide (5.8 mM).

Measurement System

40 μl of Reagent ③, 100 μl of phosphate buffered physiological saline solution (pH 7.4), and 70 μl of Test Solution ① or Test Solution ② were added to a test tube made of glass, followed by immediate stirring. The reaction mixture was suctioned into a flat cell (manufactured by Labotech Co.) and irradiated by a fluorescent lamp for one minute. Measurement of the ESR spectrum was initiated after seconds.

Comparative Measurement System (Not Containing a Singlet Oxygen Generation Reagent)

140 μl of phosphate buffered saline (pH 7.4) and 70 μl of Test Solution ① or Test Solution ② were added to a test tube made of glass, followed by immediate stirring. The reaction mixture was suctioned into a flat cell (manufactured by Labotech Co.) and irradiated by a fluorescent lamp for one minute. Measurement of ESR spectrum was initiated after 30 seconds.

Measurement Conditions of ESR Spectrum (1) Conditions common to the ESR measurement.

Measurement device: An electron spin resonance equipment, JES-RE1X (JEOL Ltd.)

Magnetic field: 337.5±5 mT

Magnetic field modulation: 100 KHz

Time constant: 0.1 second

Microwave power: 20 mW

Sweep time: two minutes

Measurement temperature: room temperature (2) ESR measurement conditions of Test Solution ①

Magnetic field modulation width: 1.25 mT (the width at which the signal of the compound of the present invention can be measured at the strongest intensity)

Receiver gain: 25

(3) ESR measurement conditions of Test Solution ②

Magnetic field modulation width: 0.1 mT (the width at which the signal of TMPD can be measured at the strongest intensity)

Receiver gain: 1000

Results

Figure 8:
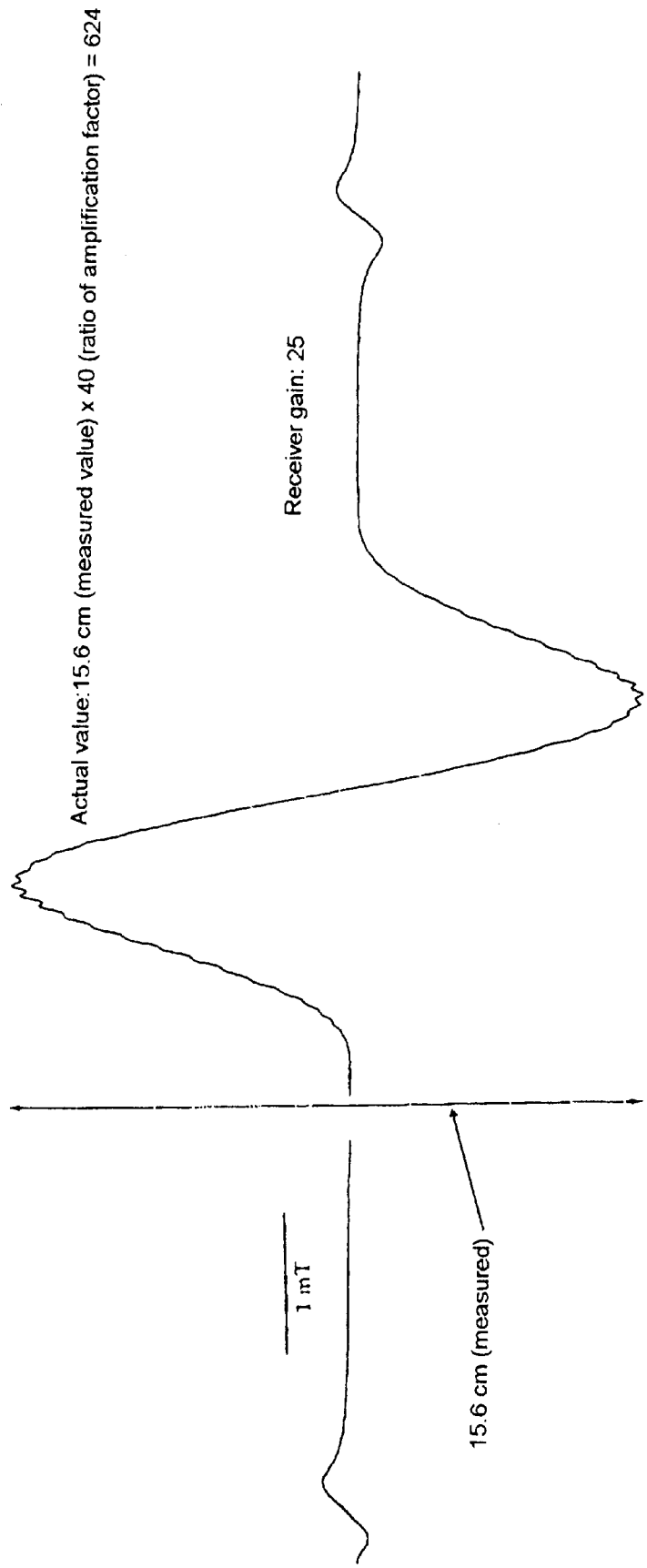
FIG. 8 shows an ESR spectrum of a solution containing singlet oxygen generation system and a test compound of 5,5'-dihydroxy-3,3'-dimethyl-1,1'-diphenyl-4,4'-bipyrazole, dissolved in a phosphate buffered saline solution (pH 7.4).
Figure 9:
FIG. 9 shows an ESR spectrum of a phosphate buffered saline solution (pH 7.4) containing only 5,5'-dihydroxy-3,3'-dimethyl-1,1'-diphenyl-4,4'-bipyrazole as a test compound.

The ESR spectrum of the measurement system for Test Solution ① (5,5'-dihydroxy-3,3'-dimethyl-1,1'-diphenyl-4,4'-bipyrazole) is shown in FIG. 8 and the corresponding ESR spectrum of the comparative system is shown in FIG. 9.

Figure 10:
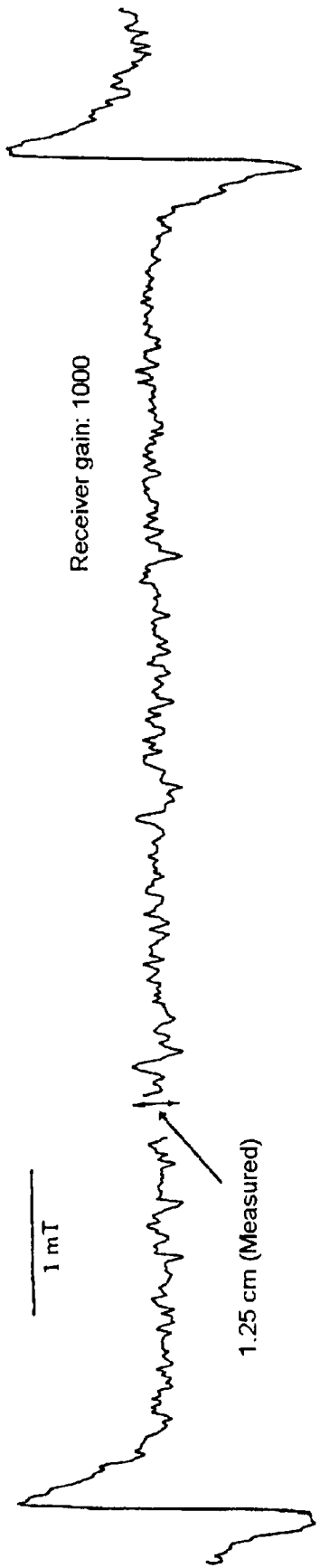
FIG. 10 shows an ESR spectrum of a solution containing a singlet oxygen generation system and TMPD as a test compound, dissolved in a phosphate buffered saline solution (pH 7.4).
Figure 11:
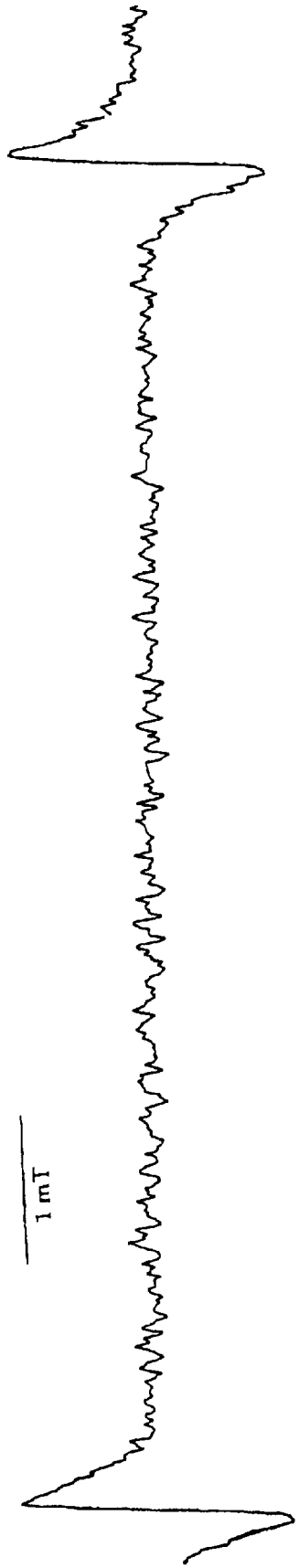
FIG. 11 shows an ESR spectrum of a phosphate buffered saline solution (pH 7.4) containing only TMPD as a test compound.

The ESR spectrum of the measurement system for Test Solution ② (TMPD solution) is shown in FIG. 10 and the corresponding ESR spectrum of the comparative system is shown in FIG. 11.

It can be seen from the signal intensity in the FIG. 8 and FIG. 10 that the signal due to capture of singlet oxygen by the compound of the present invention at pH 7.4 is about 440 times as large as the signal of TMPD solution. In other words, the sensitivity of the compound of the present invention as the detection reagent is 440 times as high as that of the typical conventional detection reagent.

The compound of the present invention can capture active oxygen and free radicals. The resulting free radicals have sufficient stability.

Because the active oxygen and free radicals produced in biological organisms cause such diseases as cerebral ischemia, heart disease, digestive system disease, carcinoma, aging, and inflammation, the compound of the present invention can be used for the prevention and medical treatment of these diseases.

Moreover, as the active oxygen and free radicals can be detected by magnetic resonance such as the ESR method which is a non-invasive measuring method by the use of the compound of the present invention, the compound of the present invention can be used as a diagnostic reagent for the diseases associated with active oxygen and free radicals such as carcinoma, ischemia, or inflammation, or a detection reagent for the active oxygen and free radical which are present in collected biological organizations, which provides useful medical information.

Obviously, numerous modifications and variations of the present invention are possible in light of the above teachings. It is therefore to be understood that within the scope of the appended claims, the invention may be practiced otherwise than as specifically described herein.

What is claimed is:

1. A medicine or reagent comprising a bipyrazole derivative of the following formula (I),

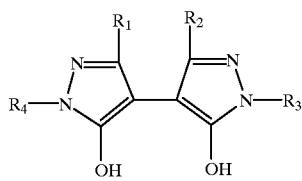

(I)

wherein $R_1$ and $R_2$ are individually a hydrogen atom, aryl group, alkyl group having 1–5 carbon atoms, or alkoxycarbonylalkyl group having a total of 3–6 carbon atoms, $R_3$ and $R_4$ are individually a hydrogen atom, alkyl group having 1–5 carbon atoms, cycloalkyl group having 5–7 carbon atoms, hydroxyalkyl group having 1–3 carbon atoms, benzyl group, naphthyl group, or substituted or unsubstituted phenyl group, as an active component.

2. The medicine or reagent according to claim 1, which is a scavenger for active oxygen or free radicals.

3. The medicine or reagent according to claim 1, which is an agent for the prevention or treatment of cerebral ischemia, heart disease, digestive system disease, carcinoma, aging, or inflammation.

4. The medicine or reagent according to claim 1, which is an agent for detection of an active oxygen or free radicals.

5. A bipyrazole derivative of the following formula (I'),

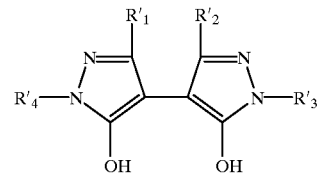

(I')

wherein $R_1'$ and $R_2'$ are individually a hydrogen atom, aryl group, alkyl group having 1–5 carbon atoms, or alkoxycarbonylalkyl group having a total of 3–6 carbon atoms, $R_3'$ and $R_4'$ are individually a hydrogen atom, alkyl group having 1–5 carbon atoms, cycloalkyl group having 5–7 carbon atoms, hydroxyalkyl group having 1–3 carbon atoms, benzyl group, naphthyl group, or substituted or unsubstituted phenyl group, provided that when both the groups $R_1'$ and $R_2'$ are a methyl group or ethoxycarbonyl group, $R_3'$ and $R_4'$ are not an unsubstituted phenyl group simultaneously, and further provided that when both of the groups $R_1'$ and $R_2'$ are a hydrogen atom, $R_3'$ and $R_4'$ are not a hydrogen atom simultaneously.

6. The bipyrazole derivative according to claim 5, wherein the groups $R_1'$ and $R_2'$ in the formula (I') are individually an alkyl group having 1–5 carbon atoms.

7. The bipyrazole derivative according to claim 5, wherein the groups $R_3'$ and $R_4'$ in the formula (I') are individually a phenyl group substituted by an alkyl group, alkoxyl group, hydroxyalkyl group, alkoxycarbonyl group, alkyl mercapto group, alkyl amino group, dialkyl amino group, halogen atom, trifluoromethyl group, nitro group, amino group, cyano group, hydroxyl group, carboxyl group, sulfonyl group, or acetamide group.

8. The bipyrazole derivative according to any one of claim 5, wherein the groups $R_3'$ and $R_4'$ in the formula (I') are individually a phenyl group substituted by an alkyl group having 1–5 carbon atoms, alkoxyl group having 1–5 carbon atoms, carboxyl group, ethoxycarbonyl group, hydroxyl group, or halogen atom.

* * * * *